(12) United States Patent
Arndt

(10) Patent No.: US 6,805,073 B2
(45) Date of Patent: Oct. 19, 2004

(54) SELF CONTAINED FINGERPRINT INK/ INKLESS REAGENT APPLICATOR AND RECORDING SUBSTRATE

(75) Inventor: Douglas C. Arndt, Jacksonville, FL (US)

(73) Assignee: Armor Holdings Forensics, Inc.

( * ) Notice: Subject to any disclaimer, the term of this patent is extended or adjusted under 35 U.S.C. 154(b) by 0 days.

(21) Appl. No.: 10/473,654
(22) PCT Filed: Mar. 5, 2003
(86) PCT No.: PCT/US03/06758
§ 371 (c)(1), (2), (4) Date: Oct. 2, 2003
(87) PCT Pub. No.: WO03/076204
PCT Pub. Date: Sep. 18, 2003

(65) Prior Publication Data
US 2004/0129205 A1 Jul. 8, 2004

Related U.S. Application Data
(60) Provisional application No. 60/362,767, filed on Mar. 8, 2002.

(51) Int. Cl.⁷ .............................................. B41M 5/165
(52) U.S. Cl. .......................................... 118/31.5; 427/1
(58) Field of Search .............................. 118/31.5; 427/1

(56) References Cited

U.S. PATENT DOCUMENTS

| | | |
|---|---|---|
| 2,500,612 A | 3/1950 | Krogh |
| 4,182,261 A | 1/1980 | Smith, III et al. |
| 4,262,623 A | 4/1981 | Smith, III et al. |
| 4,706,600 A | 11/1987 | Mason, Jr. et al. |
| 4,983,415 A | 1/1991 | Arndt et al. |
| 5,979,357 A | 11/1999 | Peavey |
| 6,488,750 B1 | 12/2002 | Arndt |
| 6,659,038 B2 * | 12/2003 | Salva Calcagno .......... 118/31.5 |

* cited by examiner

Primary Examiner—Laura Edwards
(74) Attorney, Agent, or Firm—Harold L. Jackson

(57) ABSTRACT

A self contained three sheet fingerprint applicator and recording substrate utilizes a base sheet (10) adapted to be fixed to a suitable surface, such as a package, for receiving the fingerprint, an intermediate sheet (14) with a removable section containing an ink pad (14a) infused with an ink or inkless regent compatible with the development of a fingerprint when transferred to the base sheet (10) by a person's fingerprint area and a top sheet (16) with a removable section covering the ink pad.

11 Claims, 2 Drawing Sheets

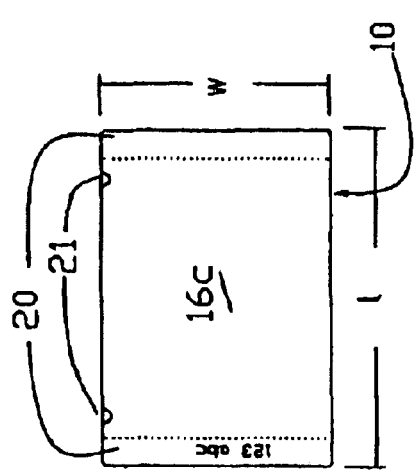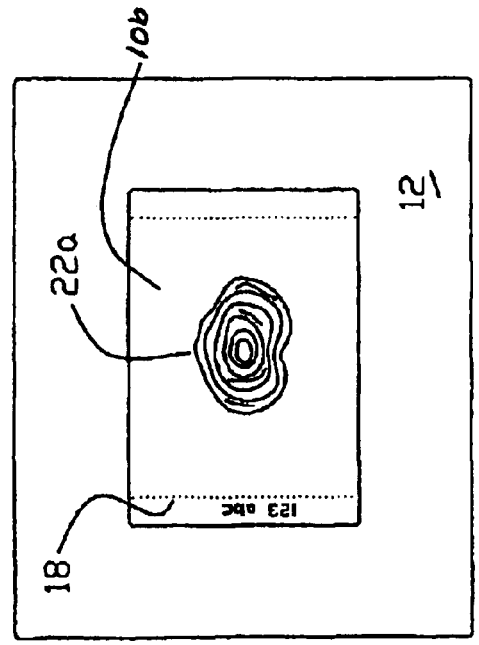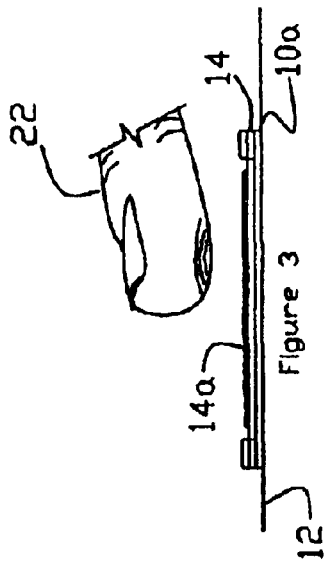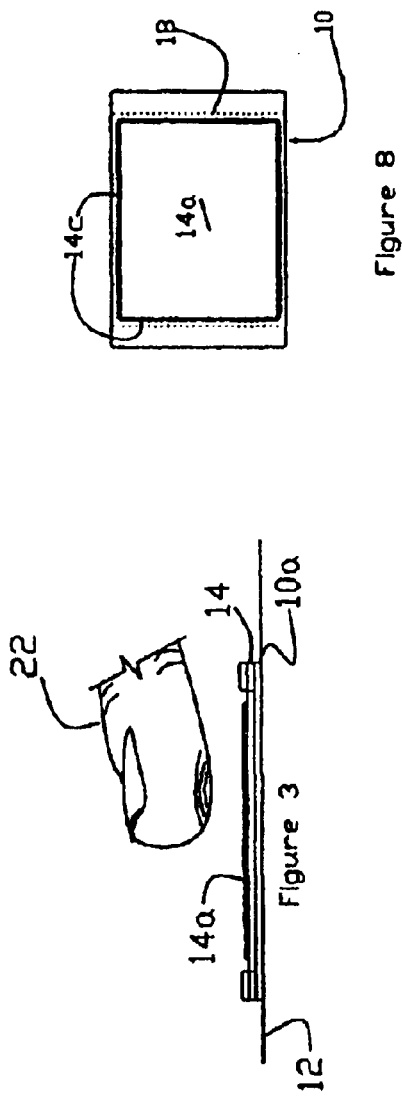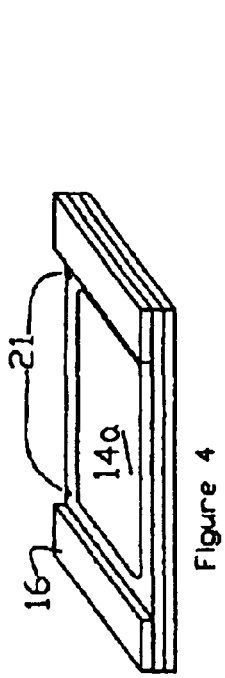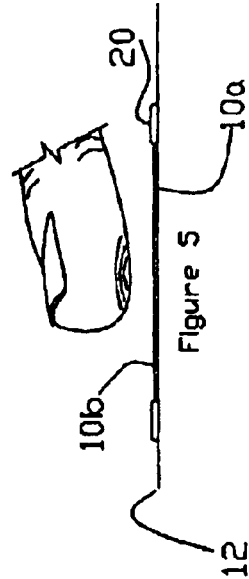

SELF CONTAINED FINGERPRINT INK/ INKLESS REAGENT APPLICATOR AND RECORDING SUBSTRATE

RELATED APPLICATION

This application claims the benefit of the filing date of provisional application No. 60/362,767, filed Mar. 8, 2002, entitled SELF CONTAINED FINGERPRINT INK APPLICATOR AND RECORDING SUBSTRATE as to all common subject matter.

FIELD OF THE INVENTION

The present invention relates to a self contained fingerprint ink applicator recording substrate. It is to be noted that, as used herein, the term "fingerprint" encompasses prints of an individual's fingers, hands or feet.

DESCRIPTION OF THE PRIOR ART

The pattern of ridge endings and ridge bifurcations (minutiae) are highly individualized and are not altered with time. The comparison of such fingerprint patterns have long been recognized as an absolute means of identifying individuals in criminal and noncriminal situations.

To obtain a person's fingerprint a chemical compound is typically applied to the person's fingerprint area and subsequently transferred to the surface of the substrate where the print is to be made. Traditionally the chemical compounds for making fingerprints are carbon based inks which comprise finely ground carbon particles suspended in a suitable liquid vehicle. Such inks are sometimes objected to because of the stain left on the person's finger.

To eliminate or greatly reduce the staining problem inkless or nonstaining ink compounds have been developed which do not rely on carbon particles to form an image of the fingerprint ridge and ridge endings.

Inkless or nonstaining ink technology has traditionally been defined as a color forming chemical reaction, between at least two reagents, that occurs at the time of fingerprint development. The chemical reaction between the two (or more) reagents provides a permanent perceivable colorant product representative of a fingerprint ridge and ridge endings pattern on the recording medium. As a general rule, the two reagents remain isolated from each other until the fingerprint is to be taken. Such nonstaining inks are sometimes hereinafter referred to as "two-phase inks".

Typically in a two-phase nonstaining ink system a first reagent (chemical compound), e.g., a color former, is applied to a person's fingertips and a second reagent, e.g., developer, capable of reacting with the first reagent to produce the colorant product, such as 8-hydroxyquinoline, is pre-applied to or inherent in the recording medium such as the paper or card receiving the print. See U.S. Pat. No. 4,983,415. Also see U.S. Pat. Nos. 4,262,623 and 4,182,261, the contents of which are incorporated herein by reference. Also see my copending PCT application entitled "Method of Recording Fingerprints on a Recording Surface Having a Thermosensitive Color Developing Layer Thereon" filed on even date herewith, the contents of which are also incorporated herein by reference.

A single-phase nonstaining ink has recently been developed by the inventor as described in U.S. Pat. No. 6,488,750 B1. In the single-phase system the two chemical reagents, i.e., a color former and developer are contained in a single reservoir but prevented from reacting while in solution by a chelating agent. This patent is also incorporated herein by reference.

Regardless of the fingerprint system used, i.e, carbon based ink, single-phase or two-phase nonstaining ink, a dispensing pad containing the appropriate ink, and an appropriate recording surface must be available to a person taking the prints. There is a need for a simple and inexpensive applicator which incorporates an ink dispensing pad and a recording surface in a single unit which will accommodate all of the above fingerprinting systems.

SUMMARY OF THE INVENTION

A self contained fingerprint ink/inkless reagent applicator, in accordance with the present invention, includes a bottom or base sheet with a adhesive affixed to the bottom thereof and an upper surface suitable for receiving a fingerprint. In the carbon based ink or single-phase nonstaining ink (inkless) system the upper surface may be plain paper. The applicator further includes a top sheet, preferably with an upper ink absorbent surface to accommodate printing and a fluid impermeable bottom surface. An intermediate sheet is sandwiched between the top and bottom sheets. The intermediate sheet contains a liquid absorbent pad, for holding an ink/inkless reagent compatible with the inking system to be employed, disposed along a portion of the upper surface thereof The lower surface of the intermediate sheet is fluid impermeable to deter the ink from migrating into the base sheet. The absorbent pad may be infused with a carbon based ink compound or a developer compound of the two-phase (inkless) system or a combined color former and developer of the single-phase (inkless) system. Where the two-phase chemistry is used the upper surface of the base sheet contains a color former otherwise it may be plain paper. Preferably an anti-wicking material is fused along the perimeter of the absorbent pad to inhibit the ink/inkless reagent from wicking out of the absorbent material during storage.

The applicator is arranged so that at least a portion of the top sheet may be readily removed to expose the ink pad for transferring ink to the fingerprint area and subsequently the portion of the second sheet ink pad to expose the recording surface of the base sheet for receiving the print.

BRIEF DESCRIPTION OF THE DRAWINGS

FIG. 1 is a top plan view of the assembled applicator of the present invention;

FIG. 3 is a side elevational view of the applicator with the top sheet removed exposing the upper surface of the ink pad and showing a finger tip positioned above the pad;

FIG. 4 is a perspective view of the applicator with the top sheet removed showing a modified ink pad;

FIG. 5 is a side elevational view of the applicator exposing the upper recording surface of the base sheet with a finger tip positioned above the surface;

FIG. 6 is a top plan view of the base sheet of the applicator with a fingerprint image on the recoding surface;

FIG. 8 is a tops plan view of an alternative arrangement, similar to FIG. 4, with the top sheet removed showing the addition of an impermeable boundary layer around the periphery of the ink/inkless reagent pad.

DESCRIPTION OF THE PREFERRED EMBODIMENT

Figure 2:
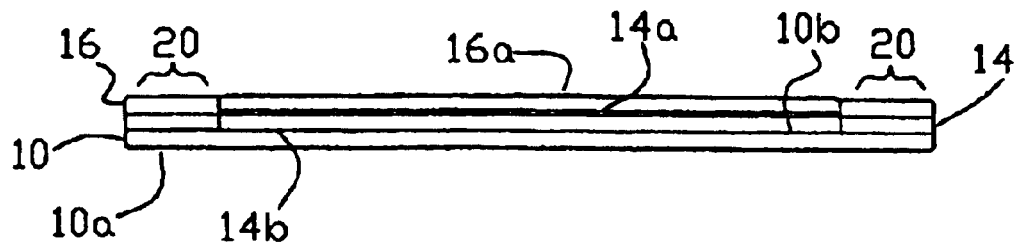
FIG. 2 is an enlarged side elevational view of the applicator of FIG. 1 illustrating the several layers thereof.
Figure 2A:
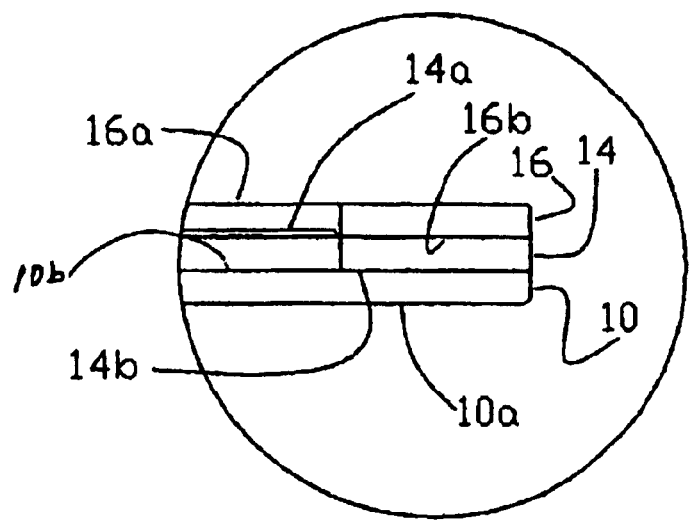
FIG. 2a is an enlarged side elevational view of the right side of the applicator of FIG. 2.

Referring now to FIGS. 1–6, a self-contained fingerprint ink/inkless reagent applicator and recording substrate in accordance with this invention includes a base or bottom sheet 10 with a conventional adhesive on the lower surface 10a thereof to enable the sheet to be affixed to a suitable surface such as a document 12, e.g., in the form of a package or document receipt, etc, The sheet 10 has an upper surface 10b suitable for receiving a fingerprint. As mentioned above, the upper surface 10a may be plain paper where the carbon based ink or single-phase chemistry is employed. With the two-phase system the upper surface 10a will include a developer or a color former.

An intermediate sheet 14, containing an upper ink/inkless reagent ("ink") reservoir/dispensing section or pad 14a, positioned between marginal end areas 20 and a bottom fluid impermeable layer 14b, is sandwiched between the bottom sheet 10 and a top sheet 16. The top sheet has an upper surface 16a, preferably suitable for absorbing ink to accommodate a printed message, trademark, etc. and a bottom fluid impermeable layer 16b. A bar code or other identifying indicia may be placed on one or both margins 20 of the top sheet so that the receipt or label with the recipient's fingerprint thereon, may readily identify the package or document delivered to the recipient. The ink pad 14a may extend completely across the width w of the sheet or be disposed in a central area thereof with ink free margins around the periphery thereof as is illustrated in FIG. 4.

As is illustrated in FIG. 8, the absorbent material forming the pad 14a extends completely across the width of the upper surface of the intermediate sheet. Also, as an optional feature, an impermeable boundary 14c extends around the perimeter of the pad 14a to inhibit the ink from wicking out of the pad during storage. The peripheral boundary 14c is imprinted on the absorbent layer 14a with an anti-wicking material such as an ultra-violet curable ink, varnish or suitable glue, preferably by using a multi-color press, and subsequently cured just before the ink or inkless reagent is printed on or applied to the absorbent layer.

The top and intermediate sheets are perforated along perforation lines 18 to permit (1) the central portion 16c of the top sheet to be easily removed to expose the ink dispensing section or layer 14a and (2) the central section of the intermediate sheet (between the margins) to be subsequently removed to expose the upper recording surface 10b of the bottom sheet so that a fingertip 22 with the ink from the ink dispensing pad thereon can be rolled or pressed thereon to provide the fingerprint image 22a. See FIGS. 3, 5, and 6. Preferably the top and intermediate sheets are notched at 21 to reduce the effort of removing these sheets during the fingerprinting process.

As briefly noted above, the chemical compound to be infused into the ink/inkless reagent dispensing layer 14a and the treatment (or lack thereof) of the upper recording surface of the base sheet will depend upon the fingerprinting system to be used. Where carbon based ink is to be used such ink may be infused into the ink dispensing layer and the upper surface of the base layer may be plain paper. Where the inkless two-phase chemistry is to be used the ink/inkless reagent dispensing layer may be infused with a suitable color former (or developer) in an appropriate solvent with the upper surface of the base layer containing an appropriate developer (or color former). For example, see my co-pending PCT application referred to above, which teaches among other suitable compounds useful in a two-phase (inkless) system, a reaction of mineral or organic acid with alcohol to form a monohydrogen or dihydrogen ester. A preferred ester, taking cost into account, is a solution of butyl dihydrogen phosphate and butyl monohydrogen phosphate having an acid activity value ("AAV") within the range of about 330 to 550 to develop a fingerprint image on a thermosensitive recording surface. If the single-phase inkless system is chosen, then the ink dispensing layer is infused with a solution of color former and developer with an appropriate amount of chelating agent and the upper surface of the base layer may be plain paper as with the carbon based ink system.

The adhesive on the lower surface of the base sheet may be a conventional pressure sensitive glue. The marginal areas of the sheets 12, 14 and 16 collectively referred to as 20 may be suitably bonded together by heat or an adhesive.

The ink dispensing layer or pad 14a may comprise a suitable absorbent material such as a thin layer of gauze or melt-blown-calendared-polyester fiber having a suitable thickness, e.g., 1.0 to 5.0 mil and preferably about 2 to 3 mil, laminated to a thin film of fluid impermeable polyester forming the intermediate sheet. Such sheet may have a thickness of about 1.5 to 2.0 mil and preferably about 1.7 mil. The top sheet may be plain paper with a suitable impermeable coating, such as lacquer or varnish, on the lower surface or may be plain paper laminated to a polyester film. As pointed out above, the bottom sheet may be plain paper for carbon based or single-phase chemistry and impregnated with a suitable color former where the two-phase chemistry is used.

Figure 7:
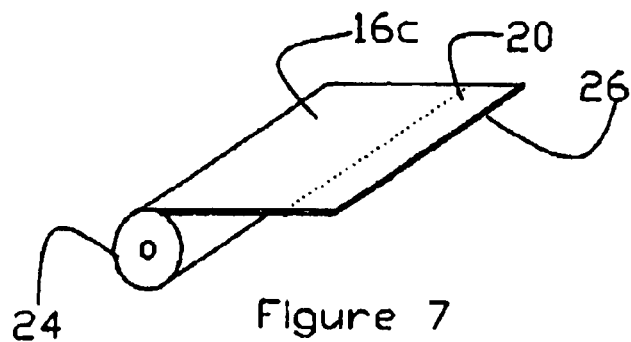
FIG. 7 is a top plan view of a group of applicators manufactured in roll form.

Multiple applicators may be manufactured in roll (24) or sheet form, e.g., like stamps, with perforations between individual applicators as is illustrated in FIG. 7. While the size of the applicator is a matter of choice, I have found that an overall length l and width w of 2.25" and 1.375", respectively, provides an excellent unit for recording prints of a person's finger tip area. A larger size larger size would be required for recording palm or footprints. The size of margin 20 is also a matter of choice, but I have found that margins 20 of about 0.3125" to be satisfactory for the 2.25"×1.375"applicator units.

There has thus been described a novel, self-contained, inexpensive and easy to use fingerprint ink applicator for applying an appropriate ink/inkless reagent to the person's fingerprint area and recording surface for receiving the print. Additions to or modifications of the invention will become apparent to those skilled in the art without involving any departure from the spirit and scope of the present invention as defined in the appended claims.

What is claimed is:

1. A self-contained fingerprint ink/inkless reagent applicator and recording surface for recording a person's fingerprint comprising:

a base sheet having a lower surface with an adhesive thereon adapted to be affixed to a suitable surface and an upper surface suitable for receiving a fingerprint;

an intermediate sheet containing an ink/inkless reagent dispensing pad on an upper surface thereof and a bottom fluid impermeable layer disposed between the ink pad and the base sheet; and a top sheet having an upper surface and a lower surface disposed adjacent the upper surface of the ink pad with a fluid impermeable layer disposed between the ink reagent pad and the top sheet, at least a portion of the top and intermediate sheets being removable, the ink reagent pad containing a chemical compound which when applied to a person's fingerprint area and deposited onto the upper surface of the recording sheet will form a colored pattern representative of the ridges and ridge endings of the fingerprint area.

2. The invention of claim 1 wherein the chemical compound is a carbon based ink.

3. The invention of claim 2 wherein the bottom sheet is paper.

4. The invention of claim 1 wherein the chemical compound includes a color former or developer and the upper surface of the bottom sheet contains a developer or color former capable of reacting with the chemical compound when deposited thereon by the person's fingerprint area to form a colorant product representing the fingerprint.

5. The invention of claim 4 wherein the chemical compound includes a developer and the upper surface of the base sheet is formed of a conventional thermosensitive paper.

6. The invention of claim 5 wherein the color former is a monohydrogen and/or dihydrogen ester.

7. The invention of claim 6 wherein the ester is a solution of butyl dihydrogen phosphate and butyl monohydrogen phosphate having a AAV within the range of about 330 to 550.

8. The invention of claim 1 wherein the chemical compound includes a color former and a developer and a chelating agent compatible with a phase two system.

9. The invention of claim 1 further including an impermeable boundary layer extending on the upper surface of the intermediate sheet and along the periphery of the ink pad.

10. The invention of claim 9 wherein the impermeable boundary layer is formed of a ultra-violet curable ink, varnish or glue.

11. The invention of claim 1 wherein the applicator includes perforations along the lateral edges thereof to allow the central sections of the top and intermediate sheets to be sequentially removed to expose a central section of the upper surface of the base sheet.

* * * * *